United States Patent [19]
de Juan, Jr. et al.

[11] Patent Number: 5,109,844
[45] Date of Patent: May 5, 1992

[54] RETINAL MICROSTIMULATION

[75] Inventors: Eugene de Juan, Jr.; Mark S. Humayun; D. Howard Phillips, all of Durham, N.C.

[73] Assignee: Duke University, Durham, N.C.

[21] Appl. No.: 595,442

[22] Filed: Oct. 11, 1990

[51] Int. Cl.$^5$ ............................................. A61N 1/05
[52] U.S. Cl. ................................. 128/419 R; 623/4; 128/784
[58] Field of Search ............... 128/419 R, 784; 623/4

[56] References Cited

U.S. PATENT DOCUMENTS

| | | | |
|---|---|---|---|
| 2,760,483 | 8/1956 | Tassicker. | |
| 3,774,618 | 11/1973 | Avery | 128/418 |
| 3,826,244 | 7/1974 | Salcman et al. | 128/2.1 E |
| 4,419,995 | 12/1983 | Hochmair et al. | 128/419 |
| 4,551,149 | 11/1985 | Sciarra | 623/4 |
| 4,611,604 | 9/1986 | Botvidsson et al. | 128/784 |
| 4,620,550 | 11/1986 | Doroshuk | 128/785 |
| 4,628,933 | 12/1986 | Michelson | 128/419 |
| 4,633,880 | 1/1987 | Osypka et al. | 128/642 |
| 4,633,889 | 1/1987 | Talalla et al. | 128/784 |
| 4,664,117 | 5/1987 | Beck | 128/420 |
| 4,682,602 | 7/1987 | Prohaska | 128/635 |
| 4,819,647 | 4/1989 | Byers et al. | 128/642 |
| 4,832,051 | 5/1989 | Jarvik et al. | 128/784 |

FOREIGN PATENT DOCUMENTS

| | | |
|---|---|---|
| 0329112 | 2/1988 | European Pat. Off. |
| 1943956 | 5/1971 | Fed. Rep. of Germany. |
| 2016276A | 4/1979 | United Kingdom. |

Primary Examiner—William E. Kamm
Assistant Examiner—Scott M. Getzow
Attorney, Agent, or Firm—Bell, Seltzer, Park & Gibson, P.A.

[57] ABSTRACT

A method for stimulating a retinal ganglion cell in a retina without penetrating the retinal basement membrane at the surface of the retina comprises: (a) positioning a ganglion cell stimulating electrode on or above the retinal basement membrane; (b) providing a ground electrode in operative association with the ganglion cell stimulating electrode, with the ground electrode positioned on or above the retinal basement membrane and positioned for capturing electric current produced by the stimulating electrode; and (c) applying a voltage to said stimulating electrode sufficient to produce an electric current which penetrates the retina and produces an action potential in a retinal ganglion cell. Apparatus for practicing the foregoing method is also disclosed.

20 Claims, 4 Drawing Sheets

RETINAL MICROSTIMULATION

FIELD OF THE INVENTION

The present invention concerns a method of stimulating retinal nerve cells and a microstimulator useful therefore.

BACKGROUND OF THE INVENTION

Numerous efforts have been made to develop aids for the blind based on conversion of optical images to auditory or tactile stimuli. However, the limited performance of such conversion devices, and the difficulty in training patients to interpret the converted signals, have seriously hampered practical application.

In the early 1930's, Foerster investigated the effect of electrically stimulating the exposed occipital pole of one cerebral hemisphere. He found that, when a point at the extreme occipital pole was stimulated, the patient perceived a small spot of light directly in front and motionless (a phosphene). Subsequently, Brindley and Lewin (1968) thoroughly studied electrical stimulation of the human occipital cortex. By varying the stimulation parameters, these investigators described in detail the location of the phosphenes produced relative to the specific region of the occipital cortex stimulated. These experiments demonstrated: (1) the consistent shape and position of phosphenes; (2) that increased stimulation pulse duration made phosphenes brighter; and (3) that there was no detectable interaction between neighboring electrodes which were as close as 2.4 mm apart.

Following the advent of intraocular surgical techniques (i.e., pars plana vitrectomy), Dawson and Radtke stimulated cat's retina by direct electrical stimulation of the retinal ganglion cell layer. These experimenters placed nine and then fourteen electrodes upon the inner retinal layer (i.e., primarily the ganglion cell layer) of two cats. Their experiments suggested that (1) electrical stimulation of the retina with 30 to 100 uA current resulted in visual cortical responses; (2) there was little increase in cortical response when stimulus currents were above 1.5 mA; and (3) there was a decline in cortical response as the stimulus current was increased. These experiments were carried out with needle-shaped electrodes which penetrated the surface of the retina (see also U.S. Pat. No. 4,628,933 to Michelson).

The possibility of implanting a more permanent intraocular prosthetic device to electrically stimulate the retina became feasible only recently after the introduction of retinal tacks in retinal surgery. De Juan et al. at Duke University Eye Center inserted retinal tacks into retinas in an effort to reattach retinas which had detached from the underlying choroid, which is the source of blood supply for the outer retina and thus the photoreceptors. See, e.g., E. de Juan et al., 99 Am. J. Ophthalmol. 272 (1985). These retinal tacks have proved to be biocompatible and remain embedded in the retina, and choroid/sclera, effectively pinning the retina up against the choroid and the posterior aspects of the globe.

While a means of attaching a retinal implant now appears in hand, there has not yet been provided an electrode suitable for chronic implant in association with the retina. Needle electrodes are difficult to fabricate individually—the possibility of fabricating a uniform bed of such electrodes would appear significantly more difficult. Moreover, penetration of the retinal surface, or basement membrane, can impart mechanical damage to the cells of the retina and the ganglion cell axons at the surface thereof. Finally, the placement of an electrode tip in close proximity to a neuron, on a chronic basis, raises the possibility of chemical damage to the neuron as a result of ion flux. Applicants are aware of nothing in the literature which obviates these problems.

SUMMARY OF THE INVENTION

A first aspect of the present invention is a method for stimulating a retinal ganglion cell in a retina without penetrating the retinal basement membrane at the surface of the retina. The method comprises: (a) positioning a ganglion cell stimulating electrode on or above the retinal basement membrane; (b) providing a ground electrode in operative association with the ganglion cell stimulating electrode, with the ground electrode positioned on or above the retinal basement membrane and positioned for capturing electric current produced by the stimulating electrode; and (c) applying a voltage to said stimulating electrode sufficient to produce an electric current which penetrates the retina and produces an action potential in a retinal ganglion cell.

In a preferred embodiment of the foregoing, a plurality of stimulating electrodes are positioned on or above the basement membrane.

A second aspect of the present invention is a retinal microstimulator for stimulating retinal ganglion cells without penetrating the retinal basement membrane at the surface of the retina. The stimulator comprises (a) a substantially flat planar basement membrane contact portion; (b) an electrode carrier having an upper and lower surface, the basement membrane contact portion connected to the electrode carrier upper surface; (c) a plurality of stimulating electrodes having upper and lower portions, the stimulating electrode lower portions connected to the electrode carrier upper surface, and with the stimulating electrode upper portions projecting outward from the electrode carrier upper surface a distance not greater than the basement membrane contact portion; and (d) a ground electrode operatively associated with each of the stimulating electrodes; the ground electrode having an upper and lower portion, with the ground electrode lower portion connected to the electrode carrier upper surface, and with the ground electrode upper portion projecting outward from the electrode carrier upper surface a distance not greater than the basement membrane contact portion.

A third aspect of the present invention is a sensory prosthesis for a vision-impaired patient which comprises a photodetector means for detecting a light signal, a retinal microstimulator as described above, and a means operatively associating the photodetector means with the retinal microstimulator for translating a light signal detected by the photodetector means into an electrical signal at the microstimulator's plurality of stimulating electrodes.

The present invention provides numerous advantages. The stimulator is easily fabricated. The surface of the retina is not penetrated by electrodes. The morbidity and mortality associated with using well-established intraocular surgical techniques in a blind eye are minimal as compared to intracranial neurosurgery. The prosthesis resides inside the eye and does not occupy another sensory modality. The high density of ganglion cells in the retina, as compared to sensory neurons in the skin, permits greater number of stimulating electrodes to be implanted in a given area. The retinal surface is relatively flat, as compared to the sulci and gyri presented on the visual cortex. The implant can be easily visualized. The current requirements to evoke phosphenes from the ganglion cells are less than those required when stimulating the cortex or optic nerve.

BRIEF DESCRIPTION OF THE DRAWINGS

The foregoing and other objects and advantages of the present invention are discussed in the following description, which should be read in conjunction with the accompanying drawings, in which.

DETAILED DESCRIPTION OF THE PREFERRED EMBODIMENTS

Figure 1:
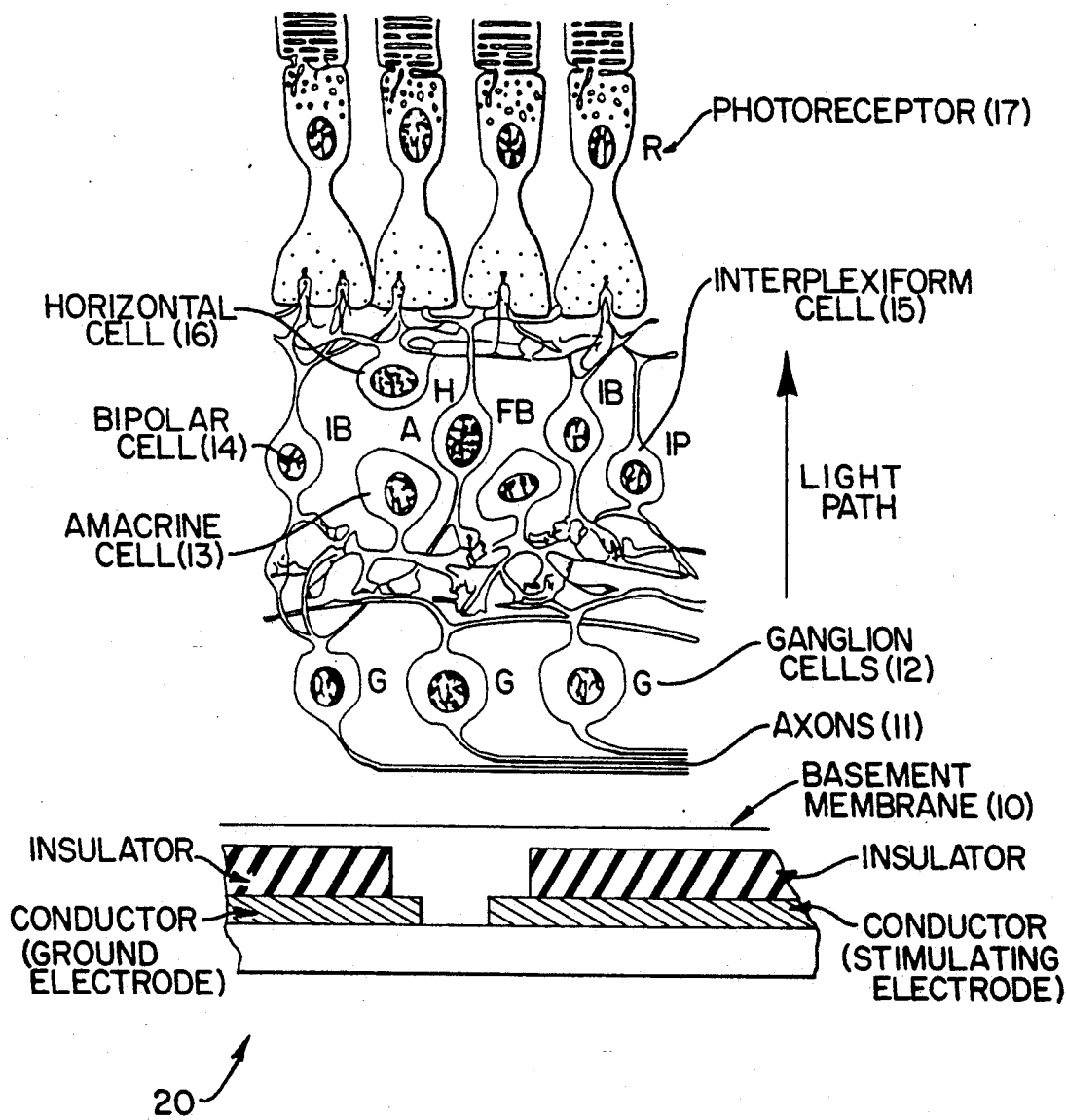
FIG. 1 is a side sectional view of a retinal microstimulator of the present invention operatively positioned above the basement membrane of a retina with the retina illustrated in substantially anatomically correct form with the natural path of light in the retina indicated by the arrow.

The method of the present invention is illustrated with one particular embodiment of the invention in FIG. which shows a retina in side-sectional view. The retinal basement membrane 10 is at the surface of the retina, above the axons 10 emanating from the retinal ganglion cells 12. The axons 11 which emanate from the retinal ganglion cells form the optic nerve (not shown), which projects to the brain. Beneath the retinal ganglion cells are nerve cells involved in intermediate signal processing, such as amacrine cells 13, bipolar cells 14, interplexiform cells 15, and horizontal cells At the back of the retina (sometimes also referred to as the "outer layer") are the photoreceptor cells 17. Note that the path of light in vivo is as indicated by the arrow, through the various nerve cells and then to the photoreceptor cells 17. In degenerative diseases of the retina, such as retinitis pigmentosa, the photoreceptor cells 17 degrade but the nerve cells, particularly the ganglion cells 12, remain viable. Thus, the present invention may be used to stimulate retinal ganglion cells in a retina where the photoreceptors are partially or fully degenerated. Note that the illustration is an approximately anatomically correct one, sufficient for the purpose of explaining the instant invention, but that the structure of the retina is variable (particularly in the fovea and the region surrounding the fovea), that nerve cells other than those illustrated may also be found in the retina, and that the anatomical and physiological bases of color vision need not be, and are not, set out for the purpose of explaining the instant invention.

Figure 2:
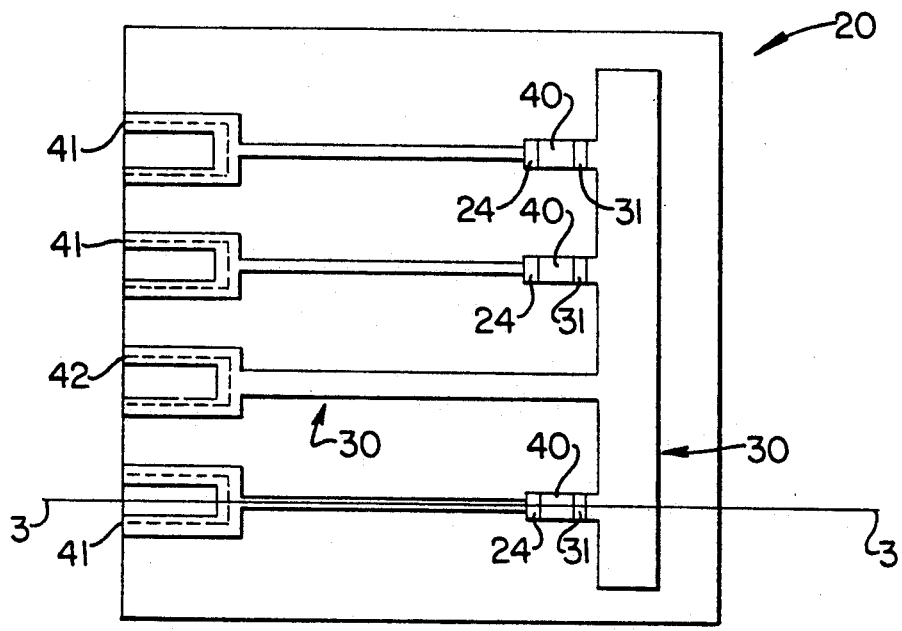
FIG. 2 is a top plan view of the retinal microstimulator illustrated in part in FIG. 1.
Figure 3:
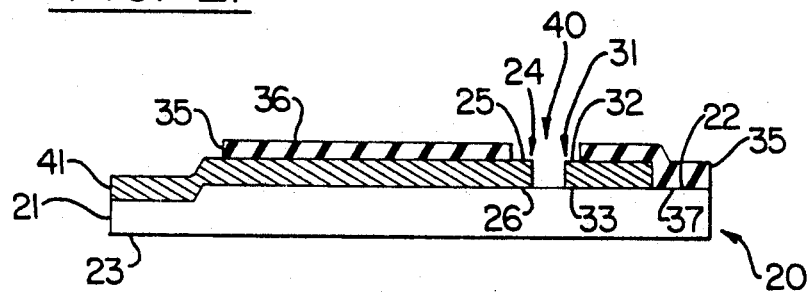
FIG. 3 is a side sectional view of the retinal microstimulator shown in FIG. 2, taken along line 3—3 in FIG. 2 (note that FIG. 1 is a fragment of FIG. 3)

A retinal microstimulator 20 is illustrated in FIG. 1 through FIG. 3. The microstimulator is built on an electrode carrier 21 having upper 22 and lower 23 surfaces. A plurality of stimulating electrodes 24 are connected to the electrode carrier. The stimulating electrodes have upper 25 and lower 26 portions, with the lower portions connected to the electrode carrier upper surface 22, and with the stimulating electrode upper portions 25 projecting outward from the electrode carrier upper surface.

A ground plane 30 provides a ground electrode 31 which is operatively associated with each of the stimulating electrodes. The ground electrodes have upper 32 and lower 33 portions, with the lower portions connected to the electrode carrier upper surface 22, and with the ground electrode upper portions projecting outward from the electrode carrier upper surface. In the illustrated embodiment there is one ground electrode paired with each stimulating electrode 24, but there could be more than one ground electrode paired with each stimulating electrode or a single ground electrode paired with multiple stimulating electrodes, so long as at least one ground electrode is operatively associated with each stimulating electrode.

An insulator 35 is connected to the electrode carrier 21, the stimulating electrodes 24, and the ground electrodes 31. The insulator has an upper 36 and lower 37 surface, with the lower surface connected to the upper portions 25 of the stimulating electrodes, the upper portions 32 of the ground electrodes, and the upper surface 22 of the electrode carrier. As explained in greater detail in connection with procedures for fabricating the retinal microstimulator, a window 40 which exposes the conductors which form the stimulating electrode and the ground electrode is etched in the insulator.

In the embodiment illustrated in FIG. 1 through FIG. 3, the upper surface 36 of the insulator forms a basement membrane contact surface. However, in alternative embodiments of the invention, because the basement membrane is soft and can become conformal, the tops of the electrodes can form the basement membrane contact surface. In addition, grooves and valleys may optionally be etched or formed in the basement membrane contact surface, so long as they do not become so acute that major projections are formed thereon which will substantially penetrate the basement membrane when the basement membrane contact surface is placed in contact therewith.

An electrical contact 41 is provided on the retinal microstimulator 20 to connect each stimulating electrode to an appropriate signal source (not illustrated). Note that a separate electrical contact 41 is provided for each stimulating electrode, while a common electrical contact 42 is provided for the ground electrodes.

Figure 4:
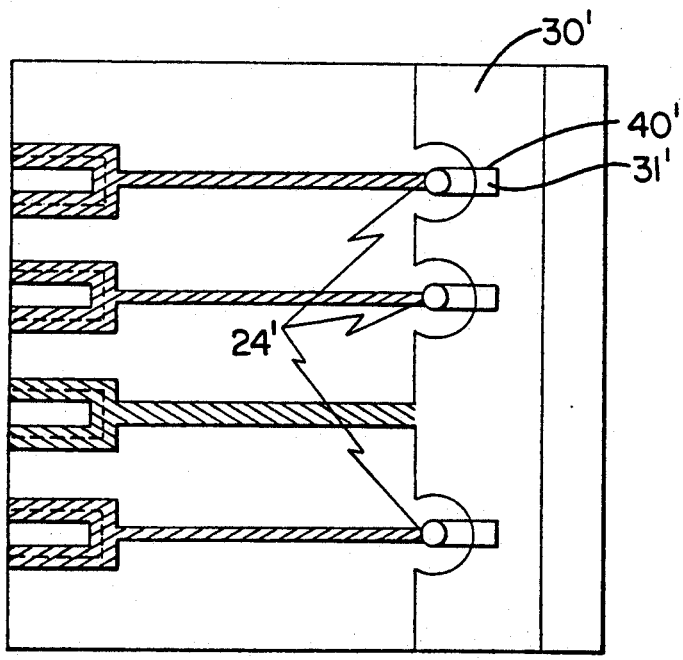
FIG. 4 is a top plan view of a second embodiment of a retinal microstimulator of the present invention.

An alternate embodiment of the present invention is shown in FIG. 4. This embodiment is essentially the same as the embodiment shown in FIGS. 1-3, except that the ground plane 30 ' is provided in a pseudo-coaxial configuration around the stimulating electrodes 24'. Note that only a portion of the ground plane is uninsulated in the region defined by the etched windows 40' formed in the insulator: the exposed portions of the ground plane are referred to herein as the ground electrodes 31'.

Retinal microstimulators according to the present invention may be fabricated by techniques conventional in the microelectronics industry. Starting with an oriented p-type or n-type silicon wafer (which will become the electrode carrier) about 10-15 mils thick, the wafer is cleaned to remove organic contaminants and native oxide. Next, good quality silicon dioxide, about 5,000 Angstroms thick, is grown on both sides of the wafer: the backside oxide is a passivant for the surface that will be in contact with the vitreous gel; the frontside oxide becomes a mask for patterning the silicon wafer. Next, silicon on the frontside is selectively etched away, using buffered hydrogen fluoride, to create a first level mask where the silicon is to be removed for V-Groove formation. Anisotropic etching of silicon in exposed areas is carried out using etchant (19:81=KOH:$H_2O$ by weight) at 80° C. for about 60 minutes so that 1.11 $\mu$m/min (100)Si is removed, {111} Si is not etched, and 30 Angstroms/minute of silicon dioxide is removed as well. The result is V-grooves about 60 $\mu$m deep (for subsequently formed electrical connections), and approximately 3000 Angstroms of oxide is left on the frontside over non-groove areas. A second level photoresist expose-and-develop process is performed to form the appropriate pattern for the electrical contacts, ground plane, stimulating electrodes, and ground electrodes. An appropriate conductor such as gold is then applied using e-beam/thermal evaporation. Metal may be removed from unwanted areas. A low temperature front surface oxide deposition step over the entire area passivates the surface and covers up the metal layer in appropriate areas for protection against body fluids: this forms the insulator layer (approximately one micron thick). Windows are etched in the oxide insulator to expose the stimulating electrodes, ground electrodes, and electrical contacts with a third level mask. Microstimulator dice are scribed and separated from the wafer, and gold wires are attached to the electrical contacts (V-grooves).

Figure 5:
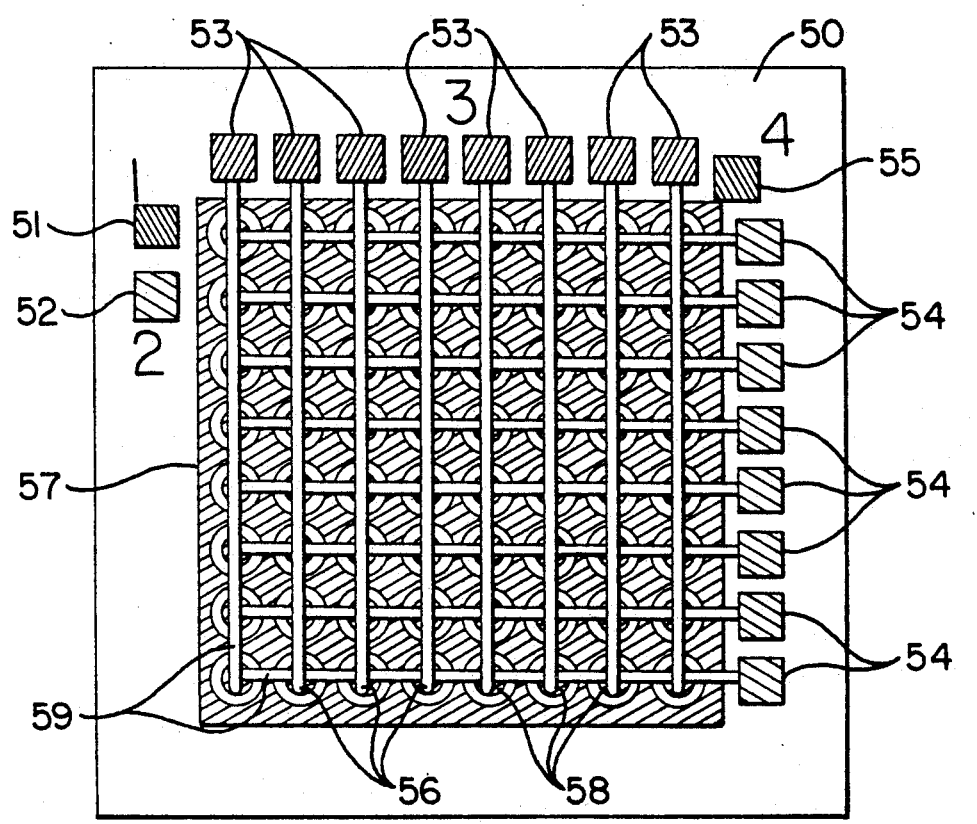
FIG. 5 is a top plan view of a third embodiment of the present invention partially cut away to show the X-Y lattice used to individually address the stimulating electrodes.

Another embodiment of the present invention which is made by conventional semiconductor fabrication techniques is shown in FIG. 5. The stimulator has a ground pad 51, a power input pad 52, stimulator steering pads in the X and Y coordinates 53, 54, and a common stimulator electrode pad 55 which is normally grounded. The ground plane 57 which surrounds the individual stimulator electrodes 56 is formed from the same metal layer used to form the stimulator electrode. Insulating gaps 58 thirty to sixty microns wide are formed by etching through the metal layer in accordance with standard techniques. The entire surface is covered with a silicon dioxide insulating layer and appropriate windows etched to provide access for electrical contact to the various pads and contacts. Sixty four windows are etched to expose each of the stimulating electrodes and an associated portion of the ground plane to provide a ground electrode, as described in connection with FIGS. 1-3 above.

In the illustrated embodiment sixty-four individual stimulator electrodes 56 are arranged in an 8 by 8 two-dimensional array. Note that the two-dimensional electrode array could take the form of numerous different patterns by staggering the electrodes, offsetting alternate rows, randomly eliminating selected electrodes in various rows or columns, etc.

Figure 6:
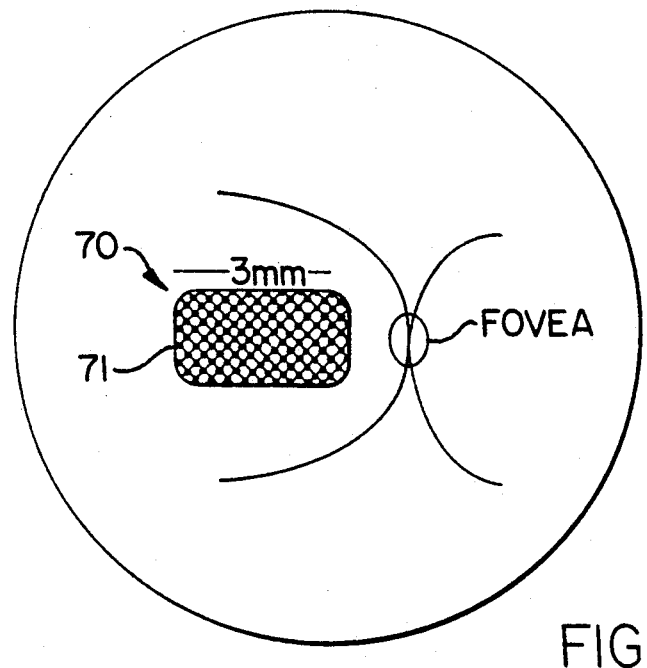
FIG. 6 is a direct view of the photodetector array of an intraocular visual prosthesis implanted on the retinal surface of an eye.

The surface of the microstimulator 50 shown is essentially planar, requiring the use of subsurface or recessed connections to the stimulator electrodes (the silicon dioxide insulator layer on the surface is only about 3000 Angstroms thick, and the metal layer is only about 7000 Angstroms to 10,000 Angstroms (1 micron) thick. Alternatively, individual connections to each of the stimulating electrodes and the ground plane could simply feed through from the backside of the chip. Transistor steering logic in the semiconductor, based on logic commonly used to address and decode semiconductor memory ICs (simply adapted for higher currents), may be used to individually address and electrically drive the stimulator electrodes 56. The embodiment shown in FIG. 6 illustrates the eight by eight X-Y lattice 59 employed to individually address the stimulating electrodes when transistor steering logic fabricated in the chip is employed.

The use of a retinal microstimulator of the present invention is shown in FIG. 1, where the stimulating electrode and the ground electrode are positioned above the retinal basement membrane. Alternatively, the stimulating electrode could be placed in direct contact with the retinal basement membrane: whether the electrode is placed on or above the retinal basement membrane is not particularly critical, so long as, when an electrical signal is applied to the stimulating electrode, the electrical signal is sufficient to produce an electric current which penetrates the retina and produces an action potential in a retinal ganglion cell.

The electrical signal provided to the stimulating electrode or electrodes should, as noted above, be one which produces an electric current capable of penetrating the retina to an excitation depth of approximately 30 micrometers, sufficient to depolarize the ganglion cells and evoke an action potential therefrom which will propagate from the ganglion cell down the axon. The waveform and frequency of this electrical potential may be varied to provide effective stimulation of visual evoked potentials with the least destructive impact on the retina. The precise nature of the electrical signal applied to the ganglion cell stimulating electrode is not a critical part of the instant invention. Preferably the electrical signal is (a) not more than about 0.3 to 3 milliamps; (b) a biphasic (+/−) waveform (avoiding direct-coupled monophasic waveforms); (c) has a pulse duration of about 0.1 to about 2 milliseconds per phase; and (d) has a frequency of about 50 to about 100 hertz. An exemplary signal is a biphasic square wave of about 2 milliamps for 1 millisecond at 60 hertz.

The ground electrode, or the unshielded portion of the ground plane, acts to both (a) project current into the retina and (b) confine or capture the electric current produced by the stimulating electrode. As discussed below, by confining or capturing the electric current produced by the stimulating electrode, the ground electrode prevents the stimulation of adjacent ganglion cells and allows a plurality of stimulating electrodes to independently stimulate those ganglion cells positioned substantially beneath each stimulating electrode. While a ground electrode must be operatively associated with each of the stimulating electrodes, the precise shape of the ground electrode within the vicinity of each stimulating electrode is not critical. For example, the ground electrode can be configured as a contact point, a set of points, as a plane, or as a coaxial ring or portion of a ring surrounding the stimulating electrode. While the shape of the flux lines of the electric current generated by the stimulating electrode will primarily be dependent on the distance between the ground electrode and the stimulating electrode, the flux line shape can also be affected by varying selectively the placement and shape of the ground electrode relative to the stimulating electrode.

Each stimulating electrode should be laterally spaced a minimum distance from the ground electrode with which it is associated to insure that the current flux lines flowing therebetween penetrate the retina to a depth sufficient to effectively stimulate the ganglion cells. This spacing will vary depending on factors such as the applied voltage (higher voltage tending to permit closer spacing) and the distance between the electrodes and the basement membrane (greater distance tending to require spacing further apart). A feature of the invention is that electrodes not substantially penetrate the retinal basement membrane. Because, as noted above, the ganglion cells are generally located about 30 microns beneath the basement membrane, the minimum spacing of electrodes will be that spacing necessary to achieve effective ganglion cell stimulation about 30 microns beneath the electrodes given the signal (voltage and waveform) applied. In general, each stimulating electrode is located not less than about 10 microns, or more preferably not less than about 20 microns, from the ground electrode with which it is operatively associated.

In one embodiment of the invention, the stimulating electrodes are laterally spaced from their associated ground electrode or electrodes in a manner which limits the ganglion cells stimulated by each stimulation electrode to only those positioned substantially below each stimulating electrode. This embodiment permits a plurality of stimulating electrodes, each capable of evoking a unique response from the retina, to be positioned on a given area of the retina. Achieving this result tends to impose a maximum on the distance between each stimulating electrode and its associated ground electrode. As discussed above, maximum spacing depends on factors such as the distance between the electrodes and the basement membrane. In a preferred embodiment of the invention, each stimulating electrode is located not more than about 200 microns, and more preferably not more than about 150 microns, from its corresponding ground electrode.

The critical resolution characteristic of electric potential delivered to the target ganglion or ganglions substantially below each stimulating electrode relative to the electric potential at other adjacent ganglions will not be critically dependent on the amplitude of the electrical potential applied to the stimulating electrode, since this ratio will be fixed by the flux line shape.

Figure 7:
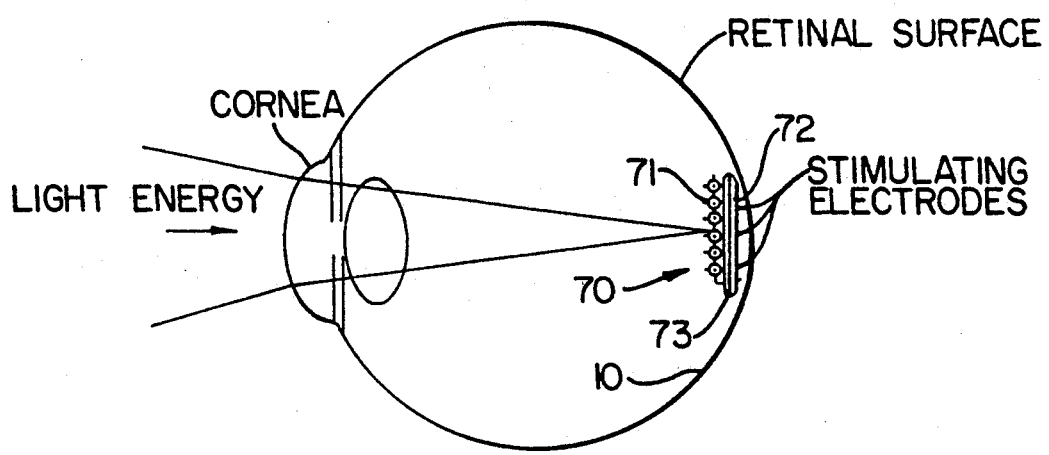
FIG. 7 is schematic side-sectional view of an eye with an intraocular visual prosthesis positioned in an eye on the retinal surface.

The retinal microstimulator of the present invention can be used with photodetectors which are also mounted in the eye, or photodetectors mounted outside of the eye. A sensory prosthesis incorporating a retinal microstimulator of the present invention and configured to be implanted in the posterior chamber of an eye is illustrated in FIGS. 6-7. The sensory prosthesis 70 comprises a photodetector array 71 serving as a photodetector means, a retinal microstimulator 72 having a two-dimensional array of electrodes as described above, and circuitry 73 interconnecting the photodetector array with the electrodes array. The electrode array of the retinal microstimulator 72 comprises sixty-four stimulating electrodes arranged in eight rows, with eight stimulating electrodes in each row, as described above.

The photodetector array 71 may be formed from a plurality of light-sensitive dipole devices, as disclosed in U.S. Pat. No. 4,628,933 (the disclosure of which is to be incorporated herein by reference). As explained in detail below, the number of individual photodetectors in the photodetector array need not equal the number of stimulating electrodes in the electrode array.

The visual prosthesis 70 may be mounted on the retina by any suitable technique, such as with an adhesive or with retinal tacks of the type used to reattach retinas which are detached from the underlying choroid. See, e.g., E. de Juan et al., 99 Am. J. Ophthalmol. 272 (1985).

Electric power may be provided to the visual prosthesis 70 by any suitable means, such as transcutaneously, by battery, by a power photocell, and by combinations thereof.

The circuitry 73 interconnecting the photodetector array may interconnect the individual photodetectors to individual stimulating electrodes in a pattern corresponding to the illumination pattern of the photodetector array, as shown in U.S. Pat. No. 4,628,933. Alternatively, the circuitry may provide for the recognition of different patterns based on the illumination pattern of the photodetector array, and then generate a signal for one ore more stimulating electrodes based on the pattern or patterns recognized. Thus, as an alternative to an approximation of vision, different phosphenes may be generated in response to level of illumination; in response to approaching objects; in response to the rate of approach of an object; in response to edges, surfaces, and points (which may be moving or stationary) and so forth. Thus, though the device may not in a particular embodiment serve as a replacement for image-sensing vision, it can provide useful information in response to light signals. Such circuitry is formed on a silicon chip by conventional microelectronics design and fabrication techniques.

The foregoing is illustrative of the present invention, and is not to be construed as limiting thereof. The invention is defined by the following claims, with equivalents of the claims to be included therein.

That which is claimed is:

1. A method for stimulating a retinal ganglion cell in a retina without penetrating the retinal basement membrane at the surface of the retina, comprising:
    (a) positioning a ganglion cell stimulating electrode on or above the retinal basement membrane;
    (b) providing a ground electrode in operative association with the ganglion cell stimulating electrode, with the ground electrode positioned on or above the retinal basement membrane and positioned for capturing electric current produced by the stimulating electrode; and
    (c) applying an electrical signal to said stimulating electrode sufficient to produce an electric current which penetrates the retina and produces an action potential in a retinal ganglion cell.

2. A method according to claim 1, wherein the stimulating electrode is located not less than about 10 microns from the ground electrode.

3. A method for stimulating a plurality of retinal ganglion cells in a retina without penetrating the retinal basement membrane at the surface of the retina, comprising:
    (a) positioning a plurality of ganglion cell stimulating electrodes on or above the retinal basement membrane, the electrodes being laterally spaced apart from one another;
    (b) providing a ground electrode in operative association with each of the ganglion cell stimulating electrodes, with the ground electrode positioned on or above the retinal basement membrane and positioned for capturing electric current produced by its associated stimulating electrode; and (c) applying an electrical signal to selected ones of said stimulating electrodes sufficient to produce an electric current which penetrates the retina and produces an action potential in retinal ganglion cells.

4. A method according to claim 3, wherein said plurality of electrodes are arranged in a two-dimensional array, and wherein a plurality of electrodes extend in each dimension of said two-dimensional array.

5. A method according to claim 3, wherein each of said stimulating electrodes is located not more than about 200 microns from said associated ground electrode.

6. A method according to claim 3, wherein each of said stimulating electrodes is spaced apart not more than about 200 microns from each adjacent stimulating electrode.

7. A method according to claim 3, wherein each stimulating electrode is located not less than about 10 microns from the operatively associated ground electrode.

8. A retinal microstimulator for stimulating retinal ganglion cells without penetrating the retinal basement membrane at the surface of the retina, comprising:

(a) a substantially flat planar basement membrane contact portion;

(b) an electrode carrier having an upper and lower surface, said basement membrane contact portion connected to said electrode carrier upper surface;

(c) a plurality of stimulating electrodes having upper and lower portions, said stimulating electrode lower portions connected to said electrode carrier upper surface, and with said stimulating electrode upper portions projecting outward from said electrode carrier upper surface a distance not greater than said basement membrane contact portion; and (d) a ground electrode operatively associated with each of said stimulating electrodes; said ground electrode having an upper and lower portion, said ground electrode lower portion connected to said electrode carrier upper surface, and with said ground electrode upper portion projecting outward from said electrode carrier upper surface a distance not greater than said basement membrane contact portion.

9. An apparatus according to claim 8, wherein each of said stimulating electrodes is located not less than about 10 microns from said operatively associated ground electrode.

10. An apparatus according to claim 8, wherein said plurality of electrodes are arranged on said electrode carrier in a two-dimensional array, and wherein a plurality of electrodes extend in each dimension of said two-dimensional array.

11. An apparatus according to claim 8 comprising sixty-four stimulating electrodes arranged in eight rows, with eight stimulating electrodes in each row.

12. An apparatus according to claim 8, wherein each of said stimulating electrodes is located not more than about 200 microns from said operatively associated ground electrode.

13. An apparatus according to claim 8, wherein each of said stimulating electrodes is spaced apart not more than about 200 microns from each adjacent stimulating electrode.

14. A sensory prosthesis for a vision-impaired patient, comprising:

(a) photodetector means for detecting a light signal;

(b) a retinal microstimulator for stimulating retinal ganglion cells without penetrating the retinal basement membrane at the surface of the retina, comprising:

(i) a substantially flat basement membrane contact portion;

(ii) an electrode carrier having an upper and lower surface, said basement membrane contact portion connected to said electrode carrier upper surface;

(iii) a plurality of stimulating electrodes having upper and lower portions, said stimulating electrode lower portions connected to said electrode carrier upper surface, and with said stimulating electrode upper portions projecting outward from said electrode carrier upper surface a distance not greater than said basement membrane contact portion; and (iv) a ground electrode operatively associated with each of said stimulating electrodes; said ground electrode having an upper and lower portion, said ground electrode lower portion connected to said electrode carrier upper surface, and with said ground electrode upper portion projecting outward from said electrode carrier upper surface a distance not greater than said basement membrane contact portion; and (c) means operatively associating said photodetector means with said retinal microstimulator for translating a light signal detected by said photodetector means into an electrical signal at said plurality of stimulating electrodes.

15. A visual prosthesis according to claim 14, wherein said photodetector means, said retinal microstimulator, and said means operatively associating said photodetector means with said retinal microstimulator are together configured to be implanted within an eye.

16. A visual prosthesis according to claim 14, wherein each of said stimulating electrodes is located not less than about 10 microns from said operatively associated ground electrode.

17. A visual prosthesis according to claim 14, wherein said plurality of electrodes are arranged on said electrode carrier in a two-dimensional array, and wherein a plurality of electrodes extend in each dimension of said two-dimensional array.

18. A visual prosthesis according to claim 14 comprising sixty-four stimulating electrodes arranged in eight rows, with eight stimulating electrodes in each row.

19. A visual prosthesis according to claim 14, wherein each of said stimulating electrodes is located not more than about 200 microns from said operatively associated ground electrode.

20. A visual prosthesis according to claim 14, wherein each of said stimulating electrodes is spaced apart not more than about 200 microns from each adjacent stimulating electrode.

* * * * *